US00PP12698P2

(12) United States Plant Patent
Moolenaar

(10) Patent No.: US PP12,698 P3
(45) Date of Patent: Jun. 11, 2002

(54) BEGONIA PLANT NAMED 'BCT9801BEG'

(75) Inventor: Alfred Nicol Moolenaar, Voorhout (NL)

(73) Assignee: BCT Bio Chemical Technologies AG, Zug (CH)

( * ) Notice: Subject to any disclaimer, the term of this patent is extended or adjusted under 35 U.S.C. 154(b) by 0 days.

(21) Appl. No.: 09/740,536

(22) Filed: Dec. 20, 2000

(51) Int. Cl.[7] ..... A01H 5/00

(52) U.S. Cl. ..... Plt./343

(58) Field of Search ..... Plt./343

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Begonia plant named 'BCT9801BEG' characterized by its compact, uniform and outwardly spreading plant habit; freely basal branching with numerous leaves per plant, dense and bushy growth habit; spiraled silvery gray and dark green leaves; and rounded leaf shape.

1 Drawing Sheet

BACKGROUND OF THE INVENTION

The present Invention relates to a new and distinct cultivar of Begonia, botanically known as *Begonia rex* hybrid, commercially known as Rex Begonia, and hereinafter referred to by the name 'BCT9801BEG'.

The new Begonia originated from a cross made by the Inventor of two unidentified selections of Rex Begonia. The cultivar BCT9801BEG was discovered and selected by the Inventor as a single plant within the progeny of the stated cross in a controlled environment in Voorhout, The Netherlands in 1997. The selection of this plant was based on its unique leaf shape, coloration and pattern.

Asexual reproduction of the new Begonia by cuttings taken in a controlled environment in Voorhout, The Netherlands, has shown that the unique features of this new Begonia are stable and reproduced true to type in successive generations.

SUMMARY OF THE INVENTION

The new Begonia has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'BCT9801BEG'. These characteristics in combination distinguish 'BCT9801BEG' as a new and distinct cultivar:

1. Compact, uniform and outwardly spreading plant habit.
2. Freely basal branching with numerous leaves per plant, dense and bushy growth habit.
3. Spiraled silvery gray and dark green leaves.
4. Rounded leaf shape.

BRIEF DESCRIPTION OF THE PHOTOGRAPH

The accompanying colored photograph illustrates the overall appearance of the new Begonia. This photograph shows the colors as true as it is reasonably possible to obtain in colored reproductions of this type. Colors in the photograph may differ slightly from the color values cited in the detailed botanical description, which accurately describe the colors of the new Begonia. The photograph comprises a top perspective view of a typical plant of 'BCT9801BEG'.

DETAILED BOTANICAL DESCRIPTION

The aforementioned and following observations, measurements and values describe plants grown in a glass-covered greenhouse in Voorhout, The Netherlands, during the winter under conditions which approximate commercial production practices. After the cuttings were rooted, plants were planted in 17-cm containers and grown for about four months with day temperatures about 19 to 21° C. and night temperatures about 17° C. In the following description, color references are made to The Royal Horticultural Society Colour Chart except where general terms of ordinary dictionary significance are used.

Botanical classification: *Begonia rex* hybrid cultivar BCT9801BEG.

Parentage: Seedling from cross-pollination of two unidentified selections of *Begonia rex* hybrid, not patented.

Propagation:

*Type*.—By cuttings.

*Time to initiate roots*.—Summer: About 21 days at 19 to 21° C. Winter: About 25 days at 19 to 21° C.

*Time to develop roots*.—Summer: About 35 days at 19 to 21° C. Winter: About 38 days at 19 to 21° C.

*Root description*.—Fine and freely branching.

Plant description:

*Plant form*.—Compact, uniform, and outwardly spreading plant habit; freely basal branching, dense and bushy.

*Plant vigor*.—Vigorous. Suitable for 13 to 17-cm containers.

*Crop time*.—To produce a finished plant in a 17-cm container, about 10 weeks are required after planting a rooted cutting.

*Branching habit*.—Very freely basal branching with about 20 to 25 leaves per plant.

*Plant height*.—About 20 cm.

*Plant width*.—About 50 cm.

Foliage description:

*Length*.—About 20 cm.

*Width*.—About 15 cm.

*Shape*.—Broadly ovate.

*Apex*.—Acuminate.

*Base*.—Asymmetrically cordate, not equilateral; lobes spirally incurved.

*Margin*.—Crenate with ciliation; undulate.

*Texture*.—Somewhat fleshy; rugose; pubescence on both surfaces.

*Color*.—Ciliation on margin: 186C. Young leaves, upper surface: Margin: Darker than 139A. Band between margin and center: 191C. Center: Darker than 139A. Young leaves, Lower surface: Margin: 187A. Band between margin and center: 138C. Center: 187A. Fully expanded leaves, upper surface: Margin: 147A. Band between margin and center: 190C. Center: 139A. Fully expanded leaves, lower surface: Margin: 59A. Band between margin and center: 138B. Center: 59A.

*Petiole*.—Length: About 15 cm. Diameter: About 6 mm. Texture: Pubescent. Color: Young leaves, 179A; fully expanded leaves, 146A.

Flower description:

*Flowering habit*.—Single flowers arranged in axillary cymes. Usually 6 to 7 flowers per cyme; up to 42 open flowers per plant at a given time. Flowers hidden under the foliage, small and inconspicuous. Flowering begins about 3 to 4 months after planting. Flowers not persistent.

*Natural flowering season*.—Plants flower from late summer until the spring in The Netherlands.

*Flowers*.—Diameter: About 7 to 10 mm. Depth (height): About 1 to 1.2 cm.

*Flower buds*.—Shape: Elliptic. Length: About 1 to 1.5 cm. Diameter: About 6 to 12 mm. Color: 146D with pubescence, 52A.

*Tepals*.—Arrangement: Four in a single whorl. Shape: Ovate. Apex: Obtuse. Margin: Entire. Length: About 1.7 to 2.4 cm. Width: About 1.3 to 1.7 cm. Color: Inner tepals, upper surface: White, close to 155D. Outer tepals, upper surface: White, close to 155D, with green, 145A, apex. Inner tepals, lower surface: White, close to 155D. Outer tepals, lower surface: White, close to 155D, with green, 145A, apices and pubescence, 52A.

*Flower bracts*.—None observed.

*Peduncles*.—Aspect: Erect. Strength: Weak. Length: About 8 to 15 mm. Color: 139C with pubescence, 52A.

*Pedicels*.—Aspect: Erect. Strength: Weak. Length: Less than 1 mm. Color: 139C with pubescence, 52A.

*Reproductive organs*.—Flowers staminate. Stamen quantity: About 30 to 60. Anther shape: Rounded. Anther length: About 1.5 mm. Anther color: 7B. Pollen: None observed.

*Seed*.—Seed production has not been observed.

Disease resistance: Plants of the new Rex Begonia have not been observed to be resistant to pathogens common to Rex Begonias.

It is claimed:

1. A new and distinct Begonia plant named 'BCT9801BEG' as illustrated and described.

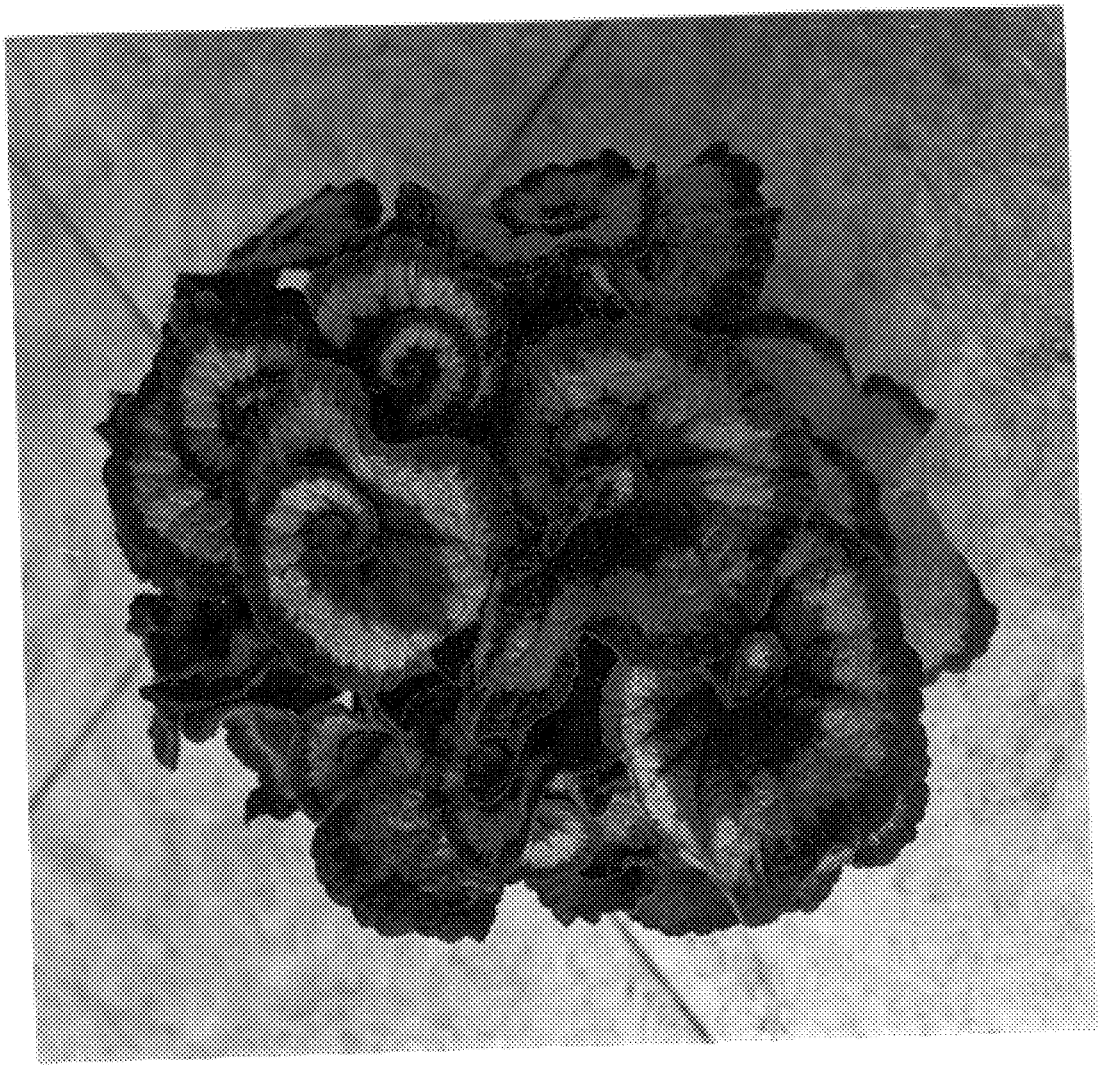

* * * * *